United States Patent [19]

Johnston et al.

[11] 4,046,514

[45] Sept. 6, 1977

[54] TEST DEVICE AND METHOD FOR DETERMINING A COMPONENT IN A SAMPLE

[75] Inventors: Katharine Gentry Johnston, Elkhart; Melvin Dee Smith, Wakarusa, both of Ind.

[73] Assignee: Miles Laboratories, Inc., Elkhart, Ind.

[21] Appl. No.: 744,703

[22] Filed: Nov. 24, 1976

[51] Int. Cl.² ............... G01N 33/16; G01N 31/14; G01N 21/06

[52] U.S. Cl. .................. 23/253 TP; 23/230 B; 195/127; 195/103.5 R

[58] Field of Search ............... 23/253 TP, 259, 230 B; 195/127, 103.5 R

[56] References Cited

U.S. PATENT DOCUMENTS

| | | | |
|---|---|---|---|
| 3,552,928 | 1/1971 | Fetter | 23/253 TP |
| 3,785,930 | 1/1974 | Ellis | 23/253 TP |
| 3,802,842 | 4/1974 | Lange et al. | 23/253 TP |
| 3,846,247 | 11/1974 | Kronish et al. | 23/253 TP |
| 3,964,871 | 6/1976 | Hochstrasser | 195/127 X |

*Primary Examiner*—R.E. Serwin
*Attorney, Agent, or Firm*—E. H. Gorman, Jr.

[57] ABSTRACT

A test device and method for determining the presence of a component in a sample are disclosed, as well as a method for making the device. The device utilizes a reactant system which produces a detectable response upon contact with the sample component, the reactant system being incorporated with a carrier matrix. The carrier matrix comprises separate filaments formed into a cloth. At least one ingredient of the reactant system is incorporated with some of the filaments prior to their being formed into the cloth. The method for making the device comprises interweaving the filaments bearing at least one reactant ingredient into a warp of other filaments, knitting the filaments into a cloth, forming a mat cloth of randomly oriented filaments or affixing the filaments to a matrix support member in a substantially parallel orientation.

29 Claims, 10 Drawing Figures

TEST DEVICE AND METHOD FOR DETERMINING A COMPONENT IN A SAMPLE

BACKGROUND OF THE INVENTION

1. Field of the Invention

The invention presently described relates to the analysis of a component in a test sample whereby a reactant system interacts with the component to produce a detectable response indicative of the presence and/or concentration of the component. More particularly, the invention relates to a carrier matrix comprised of separate filaments formed into a cloth, in which some of the filaments are incorporated with at least one ingredient of the reactant system prior to being formed into the matrix.

2. Discussion of the Prior Art

There are many test devices presently in use, especially in the medical diagnostic area, which can detect the presence of a particular component in a test sample. Besides the numerous electronic and mechanical devices useful for this purpose, one particular type of visual detection has achieved widespread recognition in the art. Thus, the so called "dip-and-read" reagent strips enjoy wide use, especially in the chemical analysis of biological fluids, because of their relative low cost, facility in use, and speed in obtaining results. Such reagent strips generally employ reactant systems impregnated in a bibulous carrier such as paper.

The bibulous carrier has taken on many forms in the prior art. For example, U.S. Pat. No. 3,846,247 teaches the use of felt, porous ceramic strips, and woven or matted glass fibers. As substitutes for paper, U.S. Pat. No. 3,552,928 teaches the use of wood sticks, cloth, sponge material, and argillaceous substances. The use of synthetic resin fleeces and glass fiber felts in place of paper is suggested in British Pat. No. 1,369,139. Another British Pat. No. 1,349,623, suggests the use of a light-permeable meshwork of thin filaments as a cover for an underlying paper matrix. This reference also suggests impregnating the paper with part of the reactant system and impregnating the meshwork with other, potentially incompatible reagents. Finally, French Pat. No. 2,170,397 teaches the use of carrier matrices having greater than 50% polyamide fibers therein.

In all of the foregoing disclosures, the reactant system (i.e., the reagents which detect the unknown component) is homogeneously impregnated into a finished matrix. Hence, in the case of cloth or woven matrices, felts, and fleeces, the ingredients of the reactant system are impregnated into the finished cloth, usually by immersion in a solution followed by drying.

Several disadvantages exist with the prior art to which the present application addresses itself. Some of the prior art devices satisfy and eliminate some of these, but none has yet been devised which jettisons them all.

One of the problems incurred by skilled artisans in the area of diagnostic test strips is that of separating mutually incompatible ingredients of a reactant system. For example, in the case of a reactant system useful in detecting occult blood in urine, it has been found that organic peroxides in the presence of an indicator such as o-tolidine will produce discoloration after long periods of storage. Another example of incompatible reagents is in the case of test strips sensitive to ketone levels in urine. In this case, the nitroprusside indicator and alkaline buffer are potentially mutually reactive. Hence, a carrier matrix capable of physically separating these ingredients from one another would be most desirable, and would greatly elevate the current state of the art.

Another void which has existed in the art is a convenient way of making a reagent strip self-calibrated. In current usage, a test strip is immersed in a urine sample and the technician must wait a predetermined time before comparing the strip with a standardized chart. The color chip on the chart which is closest to the color appearing on the test strip during the predetermined time range is indicative of the level of the component present in the system. There are many inherent disadvantages with such a procedure. Firstly, if the strip is read too late or too soon an incorrect result will ensue. Secondly, the technician reading such a strip must possess good color acuity. Even slight color blindness can cause severe inaccuracy. Thirdly, studies have shown that the results of a color comparison between a moistened strip and a standard color chart will vary somewhat from individual to individual.

The solution to this problem is a reagent strip which can be read directly without the need of recourse to an ancillary standard color chart. Thus, a strip which would read out some number or geometrical symbol indicative of the concentration of a component present in the test sample would greatly enhance accuracy and convenience of use.

Another problem encountered in reagent strips comes from the manufacturing area. Because of the great importance of accuracy in the area of analytical chemistry, it is important for manufacturers of reagent strips to keep a close watch on the quality of their products. Indeed, millions of dollars are spent each year in quality assurance programs. Products are analyzed as they leave the manufacturing area and both the stability and performance characteristics are kept under careful scrutiny. When faulty products are discovered, they are most often discarded in their entirety, thereby wasting all of the components of a particular reagent system. Surely, the state of the art would be markedly advanced if it were to become unnecessary to discard an entire batch of faulty reagent strips (and the costly reagent systems incorporated with them).

In order to address these inadequacies of the prior art, an extensive program of research and development was engaged in. A way was sought to easily separate reagents within a carrier matrix, to provide for long-term storage, to obtain better control over reagent uniformity over the entire area of a carrier matrix, and to provide a way of obtaining reagent strips which are self-calibrated. The oeuvre of these efforts is the present invention which provides a solution to each of the foregoing research goals.

SUMMARY OF THE INVENTION

Briefly stated, the present invention relates to a test device and method for determining the presence of a component in a test sample. The device utilizes the concept of a carrier matrix incorporated with a reactant system capable of interacting with a sample component to produce a detectable response. The carrier matrix comprises separate filaments forming a cloth, at least some of the filaments being substantially exclusively impregnated with at least one of the ingredients of the reactant system prior to being formed into the matrix. Thus, the device can comprise a carrier matrix having longitudinal and transverse filaments, at least an effective number of the transverse filaments being incorporated with at least one ingredient of the reactant system.

The matrix can also comprise a felt-like cloth also made of individual filaments, some of which are separately incorporated with at least one ingredient of a reactant system prior to being formed into the matrix. Hence the matrix can comprise a random orientation of the filaments. Still further, the matrix can be a cloth comprising substantially parallel oriented filaments affixed to a carrier matrix support member.

The test device of the present invention is prepared by incorporating a first plurality of filaments with at least one ingredient of the reactant system and forming the first plurality of filaments, together with a second plurality of filaments, into a cloth matrix.

DESCRIPTION OF THE DRAWINGS

The appended drawings are presented to further clarify and point out salient aspects of the present invention.

DETAILED DESCRIPTION OF THE INVENTION

Figure 1:
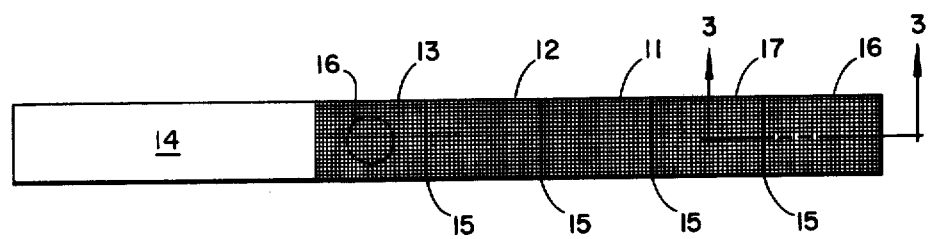
FIG. 1 shows a test device in which different reactant areas are provided.

The term "filament", as used herein, is defined as a thread-like fiber or object. Thus it includes single fibers or monofilaments, fibers which are combined (as by twisting) into threads, monofilaments which are likewise combined into threads, and threads which are themselves combined into still larger threads.

Although the composition of the filaments, as presently envisioned, is cotton in the form of thread, other compositions are equally within the scope of this invention. Thus, the filaments could conceivably comprise any natural or synthetic material which would lend itself to being formed into filaments. Cotton, wool, hemp, kapok, soy, keratin, silk, paper and zein are exemplary of natural polymers which can be formed into filaments and, subsequently, cloths. Examples of synthetic polymers similarly useful are regenerated cellulose, polyacrylates, polyolefins (such as polyethylene and polypropylene), and polyamides (such as nylon).

The ingredient or ingredients of the reactant system are incorporated with the filaments in various ways. For instance, a filament comprising many twisted fibers, such as cotton, can be drawn through a bath containing the ingredient, thereby saturating the fibers, and subsequently dried. This leaves the ingredient as a residue within the filament interstices. Another method is to bond the ingredient to the surface of the filament. Thus, hydrogen bonding or even covalent bonding between polymer filament and ingredient can be taken advantage of. In the case of extruded filaments such as polyolefins, the reactant system can be blended with the polymer in the melt prior to melt extrusion. Thus it can be seen that many techniques exist for incorporating filaments with reactant system ingredients, all of which are dependent upon the mutual properties of filament and ingredient, and all of which are determinable by a person skilled in the art.

By the phrase "at least an effective number", as such phrase relates to filaments herein, is meant that number of filaments incorporated with part of the reactant system, prior to forming the cloth matrix, necessary to produce an observable detectable response. This number can be easily ascertained by one skilled in the art. For example, if the detectable response is to be a color formed in the matrix, one merely determines the number of impregnated threads sufficient to produce an easily observable color. Likewise, where the response is the absorption or reflection of light, such as ultra-violet or visible light, enough filaments must be incorporated into the matrix so that the measurable detection range of an ultra-violet or other light sensing instrument is achieved.

The present invention lends itself to the clinical diagnosis and determinations of many test sample components. Representative of components which can be detected are pH, ion concentrations, bilirubin, urobilinogen, protein, ketones, nitrite, glucose, occult blood, and other urine components. Outside of the area of medical diagnostics, the concepts of the present invention can be applied to the determination of chlorine in industrial water systems, determining the hardness of water, measuring the relative strength of battery acid, and many other applications apparent to those skilled in the art. In applications such as those mentioned above, the presently disclosed and claimed test devices can be incorporated with many known chemistries and other reactant systems, as well as others which may arise in the future.

The unique carrier matrix which is the heart of the present invention can best be defined as a cloth. Its uniqueness, however, resides not in the fact that the matrix is a cloth, per se, but in its formation from separate filaments which are incorporated with at least part of a reactant system prior to their being formed into the cloth.

Hence, in making the matrix, the first step is to incorporate a plurality of filaments with one or more of the ingredients which comprise the reactant system. Usually this is accomplished by passing the filaments through a bath containing the ingredients so that the filaments become thoroughly saturated with the solution. The filaments are then subsequently dried to drive off the solvent.

The reactant-bearing filaments are next combined with other filaments into a cloth. This may be accomplished by weaving, knitting, matting, and other methods. Where weaving is the preferred technique, the reactant-bearing filaments can comprise the weft or filling filaments and are woven into a warp of other filaments. Conversely, the reactant-bearing filaments can comprise the warp. For this purpose, weaving techniques well-known in the art can be employed. In the case where the reactant-bearing filaments contain all of the ingredients of the reactant system, it can be seen that the concentration of the reactant system in the matrix can be controlled with extreme accuracy merely by regulating the number of reactant-bearing filaments in the weft, i.e., the weft can contain both reagent-bearing and nonreagent-bearing filaments in any desired ratio. The ratio of one ingredient of the reactant system with respect to others can be similarly controlled.

In another embodiment of this invention utilizing weaving techniques, it is possible to incorporate two or more pluralities of filaments in the weft, each plurality separately containing different ingredients of the reactant system, or different concentrations of the same ingredient.

Such an embodiment is illustrated in FIG. 1. Thus, zones 11, 12, 13, 16, and 17 represent separate woven reactant areas responsive to different concentrations of analysate in the sample. These individual areas can be separated visibly such as by colored filaments 15 and mounted by any suitable means to a matrix support member 14.

The present concept is especially usable where a reactant system contains ingredients which are potentially incompatible, and which may react with one another when homogeneously present in a carrier matrix. For example, a typical reactant system used in detecting the presence of occult blood in urine contains a redox indicator such as o-tolidine and an organic peroxide. In some prior art test devices containing these reagents, serious shelf life problems have developed because of the mutual reactivity of these components. This drawback can be overcome by incorporating each of these potentially incompatible reagents into a separate plurality of filaments. When the two sets of filaments are then woven into a warp of nonreactant-bearing filaments, the potentially incompatible reagents are effectively separated from one another, thereby greatly enhancing the shelf life of the finished matrix.

Moreover, by isolating potentially incompatible reagents in separate filaments, it is now possible to store these reagents separately in spools of filaments indefinitely, prior to their actually being formed into a cloth matrix. Whereas in the prior art, test devices are generally made in a multistep procedure, i.e., impregnation, drying, and assembly, it is now possible to perform these steps at different points in time if desired. Thus, it may be more attractive from a manufacturing standpoint to incorporate a large quantity of filaments with a reactant at one point in time and to manufacture the finished device later. This can be easily achieved using the presently disclosed concepts.

Another embodiment permits the manufacture of test devices which are self-calibrated. Thus, it is now possible to analyze a test sample or component using prior art "dip-and-read" techniques without resorting to an ancillary reference standard such as a standard color chart. For example, a test device for glucose can comprise a carrier matrix having two or more reactive areas, each area capable of producing a detectable response to a different threshold concentration of glucose, as in FIG. 1. Such systems are described in U.S. Pat. No. 2,893,844 which issued to Cook on July 7, 1959, and in U.S. Pat. No. 3,964,871 which issued to Hochstrasser on June 22, 1976. Both of these patents describe systems wherein quantities of an inhibitor, such as ascorbic acid, are present in a carrier matrix in conjunction with a color forming reactant system. The inhibitor prevents the formation of color unless a certain concentration of glucose is present. When the matrix is contacted by the sample containing glucose, the formation of color is prevented until after the inhibitor present in the matrix is consumed. Thereafter a color appears.

Hence, it can be seen that by controlling the concentration of inhibitor present in the matrix, it is possible to sense threshold concentrations of glucose present in the test sample. The disclosures of the two foregoing patents are hereby incorporated into the present specification by reference.

Figure 2:
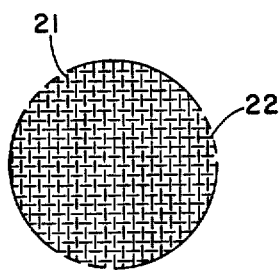
FIG. 2 is an enlarged section of an area of the carrier matrix in the test device of FIG. 1.

In one embodiment of this concept, a cloth matrix having two or more distinct reactive areas, such as is illustrated in FIG. 1, is prepared such that weft filaments (FIG. 2, filaments 21) containing the inhibitor are woven into warp filaments 22 forming each reactive area. To this end, different concentrations of inhibitor, such as ascorbic acid, are incorporated with separate pluralities of filaments. Thereafter, each of the separate pluralities is woven into individual areas 11-13, 16 and 17 of the matrix. The reagent areas can be visibly separated such as by the use of contrastingly colored filaments 15. Subsequent to the weaving in of the weft filaments incorporating the inhibitor, the entire matrix is then incorporated with the glucose-responsive reactant system. The matrix can then be attached to a suitable rigid matrix support member 14. A test device thus prepared can be directly read with respect to glucose concentration. Assuming that two reactive areas are employed, one having a higher concentration of inhibitor woven into it than the other, the device can be used to read two threshold concentrations of glucose. It can be seen that the analysis can be made more accurate by increasing the number of different reactant areas.

Figure 3:
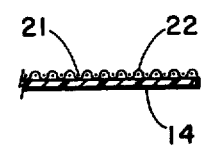
FIG. 3 shows a side view through section 3—3 of FIG. 1.

FIG. 3 clearly shows the positioning of warp threads 22 in relation to weft threads 21. It is of course in no way mandatory that variation in reactant system ingredients be achieved solely by weft, or filler, filaments. Hence, it is equally within the present invention for the reactant system ingredient to be substantially exclusively incorporated into the warp filaments.

Figure 4:
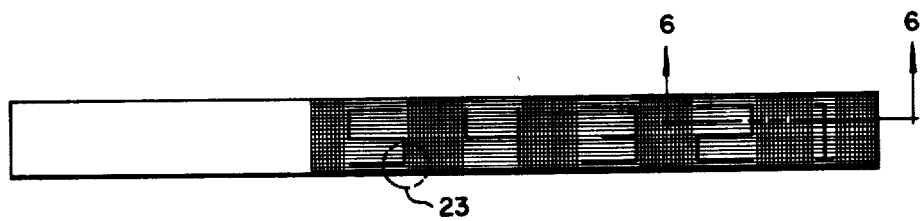
FIG. 4 presents a view of a test device of the present invention which has been self-calibrated through the use of direct numerical readout.
Figure 5:
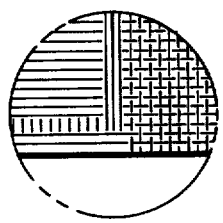
FIG. 5 is an enlarged view of the numerical readout device showing the weave pattern of the numbers on the matrix.
Figure 6:
FIG. 6 depicts a side view along section 6—6 of FIG. 4.

Another way of employing the present techniques in the creation of self-calibrated test devices is through the weaving into the matrix of specific patterns of the indicator reactant system. Thus, threads containing the reactant system can be woven into a warp in the form of arabic numerals (as in FIGS. 4, 5 and 6), geometric patterns, or other symbols. The numerals can correspond directly to the concentration of the component, can be proportional to the concentration, or otherwise representative of the amount of the component in the sample. Exemplary of geometric patterns which can be woven into the matrix are a series of "plus" signs, squares, dots, and the like. These are arranged such that the concentration of the component is a function of the number of symbols which become colored after contact with the sample. It can be seen that many variations of reactant designs woven into the matrix can be utilized, and are within the scope of the present invention.

Figure 7:
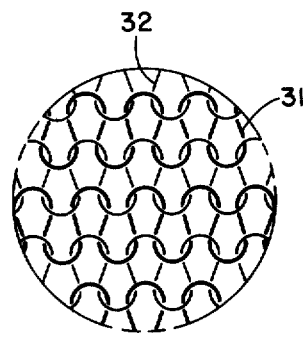
FIGS. 7 and 8 are provided to show filament interrelationship in knitting and random filament orientation, respectively.
Figure 8:
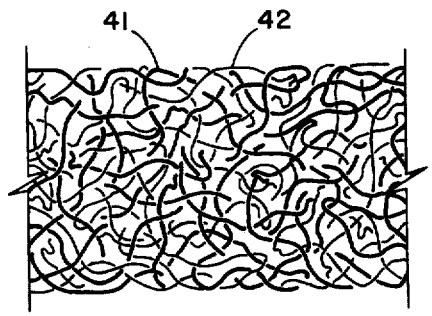
Figure 9:
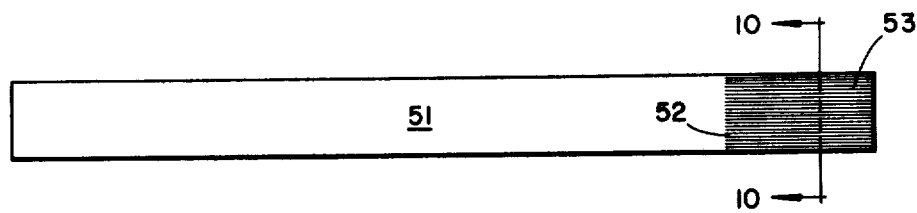
FIG. 9 is provided to illustrate an embodiment of the present invention in which the cloth matrix comprises substantially parallel oriented filaments affixed to a carrier matrix support member.
Figure 10:
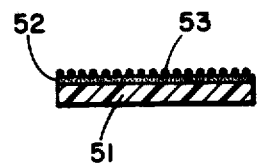
FIG. 10 shows an embodiment of the present invention wherein the matrix is a cloth comprising substantially parallel oriented threads affixed to a carrier support member.

Besides weaving, other techniques of forming the strands into the matrix can be utilized. Knitting, for example, provides a fast accurate way of forming a cloth, and reactant system-laden threads 31 (FIG. 7) can be knitted into a matrix in similar fashion as described above. Moreover, the filament strands can be randomly oriented or matted into a cloth (FIG. 8). Thus, threads 41 incorporated with a reactant system can be randomly combined with other threads 42 and compressed, heated or otherwise stressed to form a cloth. Still another way of utilizing the presently disclosed concepts is to form a cloth by affixing substantially parallel filaments to a matrix support member (FIGS. 9 and 10). Thus, a plurality of filaments, some of which are substantially exclusively incorporated with at least one ingredient of the reactant system, are combined with other filaments and affixed to a support member 51 such as a strip of polystyrene. These substantially parallel oriented filaments 53 can be affixed by any suitable means. One preferred method of affixing the filaments to the support member is through the use of an adhesive 52, such as a doubly adhesive film or tape similar to those manufactured by 3M Company.

The foregoing techniques of knitting, weaving, and other cloth forming methods require no special skills or expertise other than those presently defining the current state of the textile art. Thus standard looms and knitting machines can be used to form the presently described and claimed matrices. It is well within the ken of the skilled artisan to weave, knit or otherwise incorporate specific patterns into cloth.

The following Examples are provided to further elucidate the herein concepts of the present invention. Of course, it is to be understood that these are in no way intended as limiting the scope of the invention, nor are they to be so interpreted.

A. Examples of Self-Calibrated Test Devices

EXAMPLE I

A Self-Calibrated Glucose Test Device Having a Sewn Matrix

This Example illustrates how to prepare a self-calibrated reagent strip for use in detecting glucose in urine by sewing reagent-laden threads into a cloth. The device detects both the presence and the concentration of glucose in the sample.

Three separate reagent solutions were prepared, each responsive to the presence of glucose in urine. They each had the following composition:

| | | |
|---|---|---|
| Viscarin® (thickening agent manufactured by Marine Colloids, Inc.) | 2.5 | g |
| Plasdone® K29-32 (Polyvinylpyrrolidone available from GAF Corp.) | 25.0 | g |
| Red #4 | 0.09 | g |
| Red #3 | 0.20 | g |
| o-tolidine ·2HCl | 5.0 | g |
| Citric acid | 15.42 | g |
| Sodium citrate | 67.92 | g |
| Gantrez® AN-139 (maleic anhydride/methylvinylether copolymer manufactured by GAF Corp.) | 7.5 | g |
| Sarkosyl® (sodium lauroyl-sarcosinate manufactured by Geigy Chemical Corp.) | 2.5 | g |
| Glucose Oxidase Liquid (Glucose Oxidase L-1000, activity 950–1050 units, Takamine® Brand, Catalogue #4,622,352, available from the Marschall Division, Miles Laboratories, Inc.) | 76.0 | ml |
| Horseradish peroxidase (60 Units/mg. available from Research Products, Division of Miles Laboratories, Inc. | 0.5 | g |
| Water | 758.0 | ml |
| Ethanol | 205.0 | ml |

Enough ascorbic acid was added to the first and second solutions to achieve ascorbic acid concentrations of 250 mg/100 ml and 50 mg/100 ml., respectfully therein, and none was added to the third solution.

Each of these solutions was used to impregnate separate pluralities of cotton filaments (white, heavy duty, mercerized sewing thread, colorfast 020 manufactured by Talon, Inc.). After drying, the cotton threads were sewn into a white cotton cloth (cotton bed sheet) such that three separate reactive areas were defined: one with no ascorbic acid; another with the residue of the 50 mg % solution; and the other with the 250 mg % solution.

The sewn cotton was then cut into strips, each containing a reactive area corresponding to each impregnated plurality of filaments. Thus the matrix comprised, in vertical juxtaposition, reactive areas containing the residues 0, 50, and 250 mg % ascorbic acid solutions, respectively. Blue thread was sewn between the three areas to enhance visualization of any color response upon contacting the matrix with a glucose-bearing sample.

EXAMPLE II

A Self-Calibrated Glucose Test Device Having a Woven Matrix

This Example illustrates how to weave one form of self-calibrated carrier matrix, sensitive to both the presence and concentration of glucose in a sample such as urine.

White, mercerized, cotton thread (No. 40/3) was impregnated by dipping in a bath containing a reactant system responsive to glucose indentical as that in Example I except as indicated infra. The thread was passed through the bath at a speed of 1 meter/min. and dried at 60° C. Three baths were employed, differing from one another only in ascorbic acid concentration; one containing 250 mg/100 ml., another 50 mg %, and the third bath no ascorbic acid. Otherwise, the baths had the composition tabulated in Example I.

To form a woven carrier matrix a loom was warped with mercerized white cotton thread No. 8/4, with 16 threads per inch over a total 4 inch width. The dried, impregnated threads were then woven into the warp in the following pattern:

4 picks blue (dyed) mercerized cotton thread No. 50/3 for visualization of each reactant area.
10 picks of threads impregnated as described above (no ascorbic acid).
4 picks blue (dyed) mercerized cotton thread No. 50/3.
10 picks of threads impregnated as described above (50 mg % ascorbic acid).
4 picks blue (dyed) mercerized cotton thread No. 50/3.
10 picks of threads impregnated as described above (250 mg % ascorbic acid).
4 picks blue (dyed) mercerized cotton thread No. 50/3.

This weave sequence was repeated several times, one full sequence representing the length of a single, self-calibrated glucose test device matrix.

The woven matrix was attached to one side of 4 inch wide double-faced adhesive tape (available from 3M Co.), and then slit transversely into 4 inch long segments, each comprising one full sequence of the above weave. The segments were then attached to Tricite polystyrene sheets (available from Dow Chemical Co.) via the second side of the adhesive tape, and slit lengthwise in a paper cutter (i.e., cut parallel to the warp threads) to provide reagent strips approximately ¼ inch in width with the matrix portion being about ½ inch in length.

B. Testing the Devices of Examples I & II

EXAMPLE III

Evaluation of the Self-Calibrated Device of Example I

Test solutions were prepared by dissolving glucose in water to achieve concentrations of 25, 100 and 500 mg/100 ml glucose. Test devices prepared in accordance with Example I were tested by immersing them into these solutions.

When a test device was immersed in the 25 mg % glucose solution, only the reagent area containing no ascorbic acid exhibited reactivity, evidenced by a blue coloring in the impregnated plurality of threads). Both the top and middle reagent areas turned blue when a test device was immersed in the 100 mg % glucose solution (0 and 50 mg % ascorbic acid in the impregnated threads). Immersion in the 500 mg % glucose solution produced coloring in all three reactive areas.

EXAMPLE IV

Evaluation of the Woven Self-Calibrated Test Device

For purposes of evaluating the strips prepared in Example II, test solutions were prepared with varying glucose concentrations. In all, 5 solutions (aqueous) were prepared. Each was made 0.85% saline, the respective glucose concentrations being 100, 500, 1000, 2000, and 5000 mg/100 ml. A separate test device prepared as in Example II was immersed in each of these solutions and each device was read after 30 seconds, 1 minute and 3 minutes. The results are illustrated in the following Table.

| Glucose Mg% | Reactivity of Woven Glucose Strip in Glucose Solutions | | |
|---|---|---|---|
| | Reading Time After Immersion | | |
| | 30 sec | 1 min | 3 min |
| 100 | 1st area blue, 2nd & 3rd areas unreacted | 1st area blue, 2nd & 3rd areas unreacted | 1st area blue, 2nd area slightly blue, 3rd area unreacted |
| 500 | 1st area blue, 2nd & 3rd areas unreacted | 1st & 2nd area blue, 3rd area unreacted | 1st & 2nd area blue, 3rd area unreacted |
| 1000 | 1st area blue, 2nd area slightly blue, 3rd area unreacted | 1st & 2nd area blue, 3rd area unreacted | 1st & 2nd area blue, 3rd area slightly blue |
| 2000 | 1st area blue, 2nd area slightly blue, 3rd area unreacted | 1st & 2nd area blue, 3rd area unreacted | 1st, 2nd, and 3rd area blue |
| 5000 | 1st & 2nd area blue, 3rd area unreacted | 1st & 2nd area blue, 3rd area slightly blue | 1st, 2nd, and 3rd area blue |

1st area - no ascorbic acid
2nd area - 50 mg % ascorbic acid
3rd area - 250 mg % ascorbic acid The first reactive area of the test devices (no ascorbic acid) reacted (turned blue in color) with all five test solutions after 30 seconds. The second and third reagent areas, which contained 50 and 250 mg % ascorbic acid, respectively, showed no reactivity to the 100 mg % glucose solution at 30 seconds; the second area (50 mg % ascorbic acid) colored blue only with glucose solutions above 500 mg %; and the third area (250 mg % ascorbic acid) did not color with any of the glucose solutions at 30 seconds.

Somewhat better glucose resolution was obtained by waiting 1 minute before reading the test devices. The first reactive area colored blue at all concentrations of glucose, the second at concentrations of 500 through 2000 mg % glucose, and the third area colored only at the 5000 mg % glucose concentration, such coloration appearing only slightly after 1 minute.

The above Examples illustrate how the presently disclosed and claimed concepts can be applied to glucose analysis, but the present invention applies equally well to other analysates such as pH, ions in solution, bilirubin, urobilinogen, albumin, occult blood, nitrite, and ketone using appropriately selected, well known reagents in place of the glucose reagents described herein.

What is claimed is:

1. In a test device for determining a component in a sample, wherein a carrier matrix is incorporated with a reactant system comprising at least one ingredient, said reactant system being capable of producing a detectable response upon contact with said sample component,
   the improvement in which said matrix is a cloth comprising longitudinal and transverse filaments, at least an effective number of said transverse filaments being the only filaments in the matrix incorporated with at least one of said reactant system ingredients.

2. The improvement of claim 1 in which said reactant system comprises at least two ingredients, and said effective number of transverse filaments comprises a first plurality of filaments incorporated with at least one of said ingredients and a second plurality of filaments incorporated with at least another of said ingredients.

3. The improvement of claim 1 in which at least two of said carrier matrices are provided, each of which is incorporated with a reactant system capable of producing a detectable response to a different threshold concentration of said sample component.

4. The improvement of claim 1 in which said longitudinal and transverse filaments are interwoven.

5. The improvement of claim 4 in which said longitudinal filaments are the warp and said transverse filaments are the weft.

6. The improvement of claim 4 in which said longitudinal filaments are the weft and said transverse filaments are the warp.

7. The improvement of claim 5 in which at least two of said matrices are provided, each capable of producing a detectable response to a different threshold concentration of said component, said matrices having common warp filaments.

8. The improvement of claim 6 in which at least two of said matrices are provided, each capable of producing a detectable response to a different threshold concentration of said component, said matrices having common weft filaments.

9. The improvement of claim 1 wherein said effective number of transverse filaments present in said matrix defines at least one numerical or geometrical indicium corresponding to a predetermined threshold concentration of said component.

10. The improvement of claim 9 wherein said effective number of filaments defines at least one arabic numeral.

11. The improvement of claim 10 wherein said numeral corresponds directly to said threshold concentration.

12. The improvement of claim 9 wherein said effective number of transverse filaments define at least one geometrical indicium.

13. In a test device for determining a component in a sample, wherein a carrier matrix is incorporated with a reactant system comprising at least one ingredient, said reactant system being capable of producing a detectable response upon contact with said sample component, the improvement in which said matrix is a cloth comprising a plurality of filaments at least an effective number of which having been incorporated with at least one ingredient of said reactant system prior to formation of said cloth.

14. The improvement of claim 13 in which said filaments are substantially parallel and are affixed to a matrix support member.

15. The improvement of claim 13 in which said matrix is knitted.

16. The improvement of claim 13 in which said matrix comprises a random orientation of said filaments.

17. A test device for determining a component in a test sample wherein a carrier matrix is incorporated with a reactant system which interacts with said component to produce a detectable response, the matrix comprising first and second pluralities of knitted filaments, at least an effective number of said first plurality being the only filaments in the matrix incorporated with at least one ingredient of said reactant system.

18. The test device of claim 1 in which said component is glucose, bilirubin, urobilinogen, albumin, ketone, occult blood, nitrite, hydrogen ion, or cholesterol.

19. The test device of claim 13 in which said component is glucose, bilirubin, urobilinogen, albumin, ketone, occult blood, nitrite, hydrogen ion, or cholesterol.

20. The test device of claim 17 in which said component is glucose, bilirubin, urobilinogen, albumin, ketone, occult blood, nitrite, hydrogen ion, or cholesterol.

21. In a method for preparing a test device for determining the presence of a component in a sample wherein a cloth carrier matrix is incorporated with a reactant system capable of interacting with said component to produce a detectable response, the improvement which comprises incorporating at least one ingredient of said reactant system with at least one first filament, and forming a cloth matrix comprising said first filament and a plurality of second filaments.

22. The improved method of claim 21 in which said cloth matrix is formed by weaving.

23. The improved method of claim 21 in which said cloth matrix is formed by knitting.

24. The improved method of claim 21 in which said cloth matrix is formed by stressing a random orientation of said first and second filaments to produce a cloth matrix of randomly oriented filaments.

25. The improved method of claim 21 in which said cloth matrix is incorporated with remaining ingredients of said reactant system.

26. A method for preparing a test device for determining the presence of a component in a sample wherein a cloth carrier matrix is incorporated with a reactant system capable of interacting with said component to produce a detectable response, said method comprising incorporating at least one ingredient of said reactant system with a plurality of first filaments, incorporating remaining ingredients of said reactant system with a plurality of second filaments, and forming a cloth matrix from said first and second filaments.

27. The method of claim 26 in which said cloth matrix is formed by weaving.

28. The method of claim 26 in which said cloth matrix is formed by knitting.

29. The method of claim 26 in which said cloth matrix is formed by stressing a random orientation of said first and second filaments to produce a cloth matrix of randomly oriented filaments.

* * * * *